(12) United States Patent
Ahuja et al.

(10) Patent No.: US 7,238,527 B2
(45) Date of Patent: Jul. 3, 2007

(54) **METHODS AND COMPOSITIONS FOR RAPID *IN VITRO* PROPAGATION OF *SWERTIA CHIRATA***

(76) Inventors: Ashok Ahuja, Regional Research Laboratory Jammu, Canal Road, Jammu (IN) 180 001; Sushma Koul, Regional Research Laboratory Jammu, Canal Road, Jammu (IN) 180 001; Brij Lal Kaul, Regional Research Laboratory Jammu, Canal Road, Jammu (IN) 180 001; Navin Kumar Verma, Regional Research Laboratory Jammu, Canal Road, Jammu (IN) 180 001; Mahraj Krishen Kaul, Regional Research Laboratory Jammu, Canal Road, Jammu (IN) 180 001; Ravinder Kumar Raina, Regional Research Laboratory Jammu, Canal Road, Jammu (IN) 180 001; Ghulam Nabi Qazi, Regional Research Laboratory Jammu, Canal Road, Jammu (IN) 180 001

( * ) Notice: Subject to any disclaimer, the term of this patent is extended or adjusted under 35 U.S.C. 154(b) by 1 day.

(21) Appl. No.: 10/917,919

(22) Filed: Aug. 13, 2004

(65) Prior Publication Data
US 2005/0019920 A1    Jan. 27, 2005

Related U.S. Application Data

(62) Division of application No. 10/011,208, filed on Nov. 30, 2001, now Pat. No. 6,855,547.

(51) Int. Cl.
*C12N 5/02* (2006.01)

(52) U.S. Cl. .................. 435/431; 435/410; 435/420; 435/430; 435/430.1

(58) Field of Classification Search .............. 435/410, 435/420, 431, 430, 430.1
See application file for complete search history.

(56) References Cited

U.S. PATENT DOCUMENTS

| | | | | |
|---|---|---|---|---|
| 4,666,844 | A * | 5/1987 | Cheng | 435/424 |
| 5,244,794 | A * | 9/1993 | Prince et al. | 435/113 |
| 5,908,771 | A * | 6/1999 | Liu et al. | 800/278 |
| 6,492,174 | B1 * | 12/2002 | Pullman et al. | 435/422 |
| 6,563,024 | B1 * | 5/2003 | Kawazu et al. | 800/294 |
| 6,849,453 | B2 * | 2/2005 | Neelwarne et al. | 435/410 |
| 6,855,547 | B2 * | 2/2005 | Ahuja et al. | 435/420 |

FOREIGN PATENT DOCUMENTS

WO    WO 03/045132    6/2003

OTHER PUBLICATIONS

Nalawade SM et al., 2003, "Studies on tissue culture of Chinese medicinal plant resources in Taiwan and their sustainable utilization" *Bot. Bull. Acad. Sin.* 44:79-98.

Chang C et al., 2000, "A tissue culture protocol for propagation of a rare plant, *Lilium speciosum* Thunb. var. *Gloriosoides* Baker" *Bot. Bull. Acad. Sin.* 41:139-142.

Keil, M et al., 2000, "Production of amarogentin in root cultures of *Swertia chirata*" *Plant Med.* 66:452-457.

Wawrosch, C et al., 1999, Micropropagation of the threatened Nepalese medicinal plant *Swertia chirata* Buch.-Ham. ex Wall. *Plant Cell Reports* 18:997-1001.

Kitamura YH et al., 1989, "Plant regeneration from callus cultures of *Swertia pseudochinensis*" *Shoyakugaku Zasshi* 43:256-258.

Kitamura YH et al., 1988, "Production of swertiamarin in cultured tissues of *Swertia pseudochinensis*" *Chem. Pharm. Bull.* 36:1575-1576.

Kirtikar KM, Basu BD, 1980, Indian Medicinal Plants, Bishen Singh Mahendrapal Singh, Dehradun, table of contents.

Kirtikar KM, Basu BD, 1980, Indian Medicinal Plants, Bishen Singh Mahendrapal Singh, Dehradun, pp. 1651-1671.

Chopra RN et al., 1958, Indigenous Drugs of India. U.N. Dhur & Sons Private Limited, Calcutta, table of contents and p. 250.

Murashige T et al., 1962, "A revised medium for rapid growth and bioassays with tobacco tissue cultures" *Physiol. Plant* 15:473-493.

Dalal SR, Shah RG, Jul. 7, 1956, "Swerchirin, a new xanthone from *Swertia chirata*" *Chemistry and Industry* p. 664.

Korte F, Schicke HG, 1956, "Zur chemischen klassifizierung von pflanzen, XII mitteil: zur kenntnis des amarogentins" *Chem. Ber.* 89:2404-2408.

(Continued)

*Primary Examiner*—L B Lankford
(74) *Attorney, Agent, or Firm*—Baker Botts L.L.P.

(57) ABSTRACT

The present disclosure relates to methods and compositions for in vitro cultivation of species of *Swertia*, e.g. *Swertia chirata* (Ham.). The disclosure provides culture media comprising Murashige and Skoog (MS) basal culture medium, plant hormones preferably selected from the group consisting of benzyladenine (BAP), gibberellic acid ($GA_3$), and auxins, and other additives, e.g. sucrose and agar. Preferably, auxins are selected from the group consisting of indole acetic acid (IAA), indole butyric acid (IBA), and naphthalene acetic acid (NAA). Individual plant hormone concentrations are preferably from about 0.5 mg/L to about 5.0 mg/L. The disclosure provides methods of in vitro cultivation of *Swertia chirata* comprising contacting preferably axillary bud and/or shoot apex explants with an initiation medium comprising a modified MS basal culture medium, BAP, IAA, IBA, and NAA to produce a primary explant, contacting the primary explant with a shoot propagation medium comprising, a modified MS basal culture medium, BAP, $GA_3$, and IAA to produce a secondary explant, contacting a secondary explant with a rooting medium comprising a modified MS basal culture medium, IAA, IBA, and NAA. The methods and compositions of the invention are capable of inducing extraordinarily rapid in vitro propagation of *Swertia chirata*. The methods and compositions of the disclosure may be useful for conservation of this threatened species as well as producing bulk quantities, e.g. gram, kilogram or more, of plant material for medicinal

6 Claims, 4 Drawing Sheets
(4 of 4 Drawing Sheet(s) Filed in Color)

OTHER PUBLICATIONS

Korte F, 1955, "Amarogentin, ein neuer Bitterstoff aus Gentianaceen: charakteristsche pflanzeninhaltsstoffe, IX mitteil" *Chem. Ber.* 88:704-707.

Saxena et al., Micropropagation of Psoralea corylifolia. Journal of Medicinal and Aromatic Plant Sciences 1998, vol. 20: No. 1, pp. 15-18.

Mohan Vandna et al., In vitro micropropagation of Moringa pterygosperma, Phytomorphology 1995, vol. 45: No.3-4, pp. 253-261.

Amin et al., Rapid clonal propagation of Guava through in vitro shoot proliferation on nodal explants of mature trees, Plant Cell Tissue and Organ Culture, 1987, vol. 9: No. 3, pp. 235-244.

* cited by examiner

METHODS AND COMPOSITIONS FOR RAPID IN VITRO PROPAGATION OF SWERTIA CHIRATA

This application is a divisional of U.S. patent application Ser. No. 10/011,208 filed on Nov. 30, 2001, now U.S Pat No. 6,855, 547 which is incorporated by reference in its entirety herein.

FIELD OF THE INVENTION

The present invention relates to novel culture media compositions for rapid in vitro propagation of *Swertia chirata*, a threatened plant species. Culture media of the invention comprise a modified Murashige and Skoog (MS) basal culture medium and various plant hormones. The particular compositions lead to extraordinarily rapid in vitro propagation of specific parts of *Swertia chirata*. Mass propagation of the plant using compositions of the invention may be achieved by using axillary buds and shoot apices in the in vitro culture media. The present invention also relates to methods of rapid in vitro propagation of *Swertia chirata*.

BACKGROUND OF THE INVENTION

*Swertia chirata* (Ham) of the Gentianaceae family is a slender, upright herb found in the Himalayas from Kashmir to Bhutan and Khasi Hills. The plants is an erect herb, stems are robust 0.6 to 1.5 m, branching leaves are opposite, broadly lanceolate, acute, lower leaf often much larger, sometimes petioled. Calyx and corolla are four-lobed. The corolla is green-yellow and tinged with purple. See Kirtikar K M, Basu B D, 1985, Indian Medicinal Plants, Bishen Singh Mahendrapal Singh, Dehradun.

The whole plant contains gentiamine alkaloids and the aerial part contains xanthones. The main chemical constituents of this plant are ophelic acid and chiratin. The plant also contains resins, tannin, gum, carbonates, phosphates and 4 to 6 per cent ash. See Kirtikar K M, Basu B D, 1985, Indian Medicinal Plants, Bishen Singh Mahendrapal Singh, Dehradun; Chopra RN, 1982, Indigenous Drugs of India. Academic Publishers, Calcutta. A number of workers have shown that the drug contains bitter glycosidal components, chiratin and amarogentin, swerchirin, phytosterol, also a number of acids and phenolic compounds. See Korte F, 1955, Chem. Ber. 88:704; Rorte F, Schicke H G, 1956, Chem. Ber. 89:2404; Dalall S R, Shah R G, 1956, Chemistry and Industry 664.

*Swertia* species are known for their medicinal value. The Wealth of India, Raw materials Vol X PID (CSIR) New Delhi provide in detail full account of distribution economic importance and uses of genus *Swertia*. For example, aqueous extracts of *Swertia* may be used during fever. Other uses include bronchial asthma, dyspepsia and debility. It is a favourite remedy in intermittent fevers, acidity and in bilious dyspepsia accompanied by fever. *Swertia chirata* is a valuable medicinal plant.

Due to its high demand by the pharmaceutical industry in India and the world, the species has been extensively exploited, so much so that it is now listed a threatened species.

Presently, supply depends on wild sources that have been depleted by over harvesting and progressive habitat clearance. It would, therefore, be helpful to use a tissue culture procedure for large scale propagation and conservation. Beside the strategy evolved should maintain quality and homogeneity of herbs.

Miura et al. (1978) has reviewed the work on in vitro regeneration and the production of secondary metabolites in *Swertia pseudochinensis* and *Swertia Japonica*. These workers have described organogenesis from the callus cultures of *S. japonica* and *S. pseudochinensis* as well as production of Swertiamarin in cultured tissues of *S. pseudochinensis*.

Recently, Keil et al. reported production of Amarogentian in root cultures of *Swertia chirata* from untransformed and transformed root cultures. (Keil et al. 2000 Planta Med, 452–457). Regeneration using root explants has recently been described by Wawrosch et al. (1999).

The roots which formed under the regenerated shoots were short and swollen requiring modification of rooting procedure for better survival rate in the field (Wawrosch C C, Maskay N and Kopp B (1999) Plant Cell Rep. 18:997–2001). Therefore, new media formulation(s) that are capable of efficient plant regeneration in vitro for mass propagation of *Swertia chirata* are desirable.

SUMMARY OF THE INVENTION

The present invention relates to methods and compositions for rapid in vitro cultivation of species of *Swertia*, e.g. *Swertia chirata* (Ham). The invention provides culture media comprising MS basal culture media and plant hormones, preferably selected from the group consisting of indole acetic acid (IAA), indole butyric acid (IBA), gibberellic acid ($GA_3$), benzyladenine (BAP), and naphthalene acetic acid (NAA). The invention provides methods of *Swertia* propagation comprising:

contacting a *Swertia* explant with a first medium comprising MS basal culture medium I, from about 0.5 mg/L to about 1.0 mg/L benzyladenine, from about 0.5 mg/L to about 1.0 mg/L indole acetic acid, from about 0.5 mg/L to about 1.0 mg/L indole butyric acid, about 0.5 mg/L naphthalene acetic acid, and from about 1% to about 3% sucrose to produce a primary explant;

contacting this primary explant with a second medium comprising MS basal culture medium I, from about 0.5 mg/L to about 1.0 mg/L benzyladenine, about 1.0 mg/L indole acetic acid, about 1.0 mg/L gibberellic acid, and from about 1% to about 3% sucrose to produce a secondary explant; and contacting this secondary explant with a third medium comprising MS basal culture medium I, about 1.0 mg/L indole acetic acid, about 1.0 mg/L indole butyric acid, about 1.0 mg/L naphthalene acetic acid, and from about 1% to about 3% sucrose to produce a tertiary explant.

The methods and compositions of the invention are suitable for use with axillary buds and shoot apices. The methods and compositions of the invention are further suitable for mass propagation of *Swertia*. The methods and compositions may be used to achieve consistent plant growth over several generations.

BRIEF DESCRIPTION OF THE DRAWINGS

The patent application file contains at least one drawing executed in color. Copies of this patent or patent application publication with color drawing(s) will be provided by the United States Patent and Trademark Office upon request and payment of the necessary fee.

DETAILED DESCRIPTION OF THE INVENTION

Figure 1:
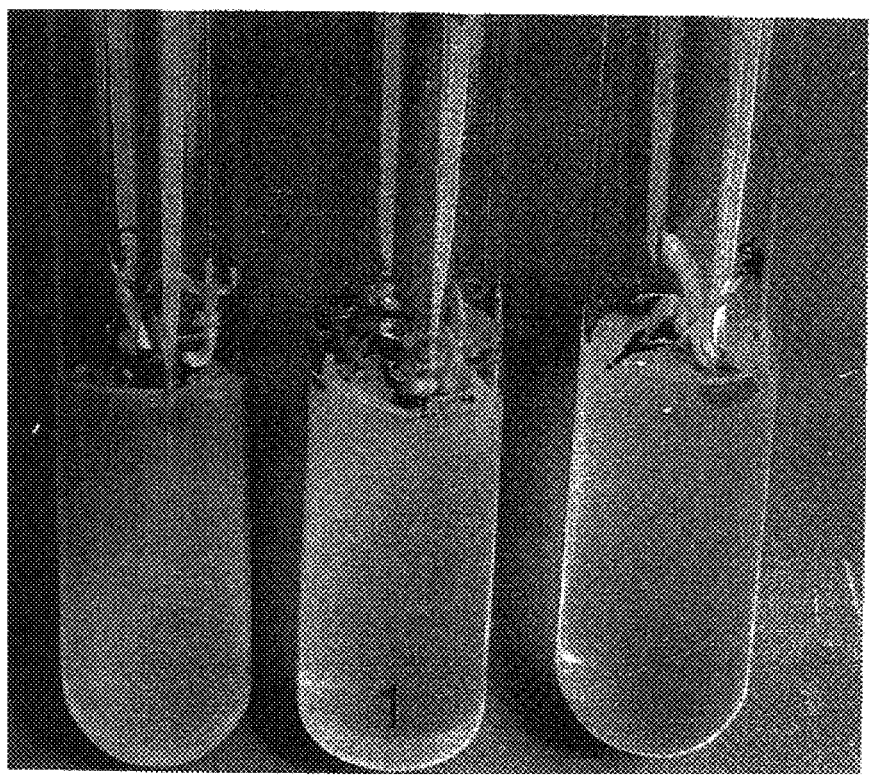
FIG. 1. Explants obtained from *Swertia chirata* shoot apices and axillary buds in response to tissue culture media formulations of the invention.
Figure 2A:
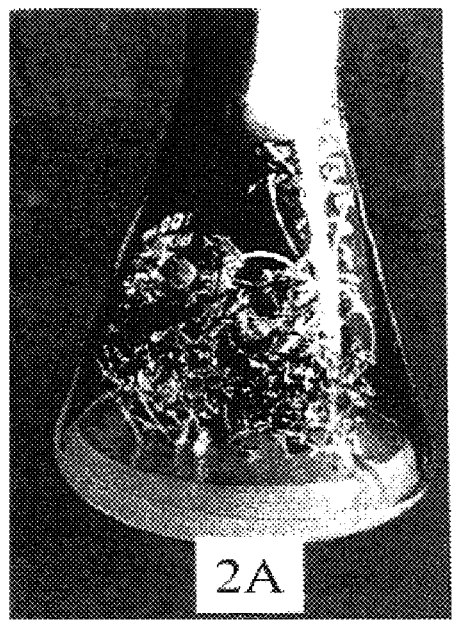
FIG. 2. Proliferation of multiple shoots on media comprising (A) modified MS basal culture media, 0.5 mg/L BAP and 1.0 mg/L $GA_3$ or (B) modified MS basal culture media, 1.0 mg/L IAA and 3% sucrose.
Figure 2B:
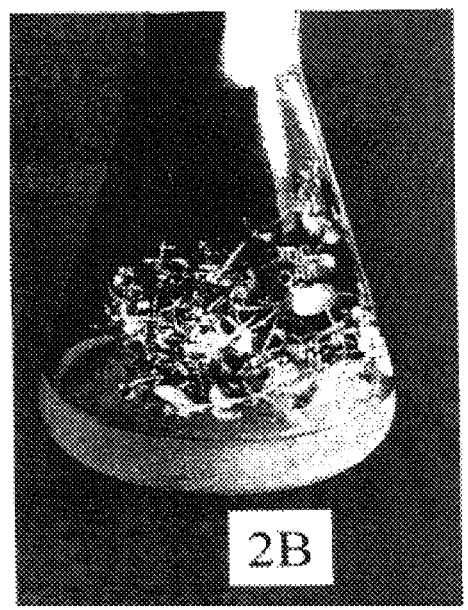
Figure 3:
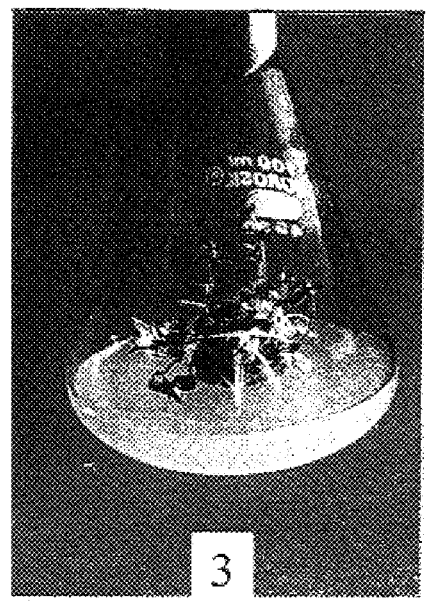
FIG. 3. Root induction at the base of in vitro shoot on media comprising modified MS basal culture media and IAA.
Figure 4:
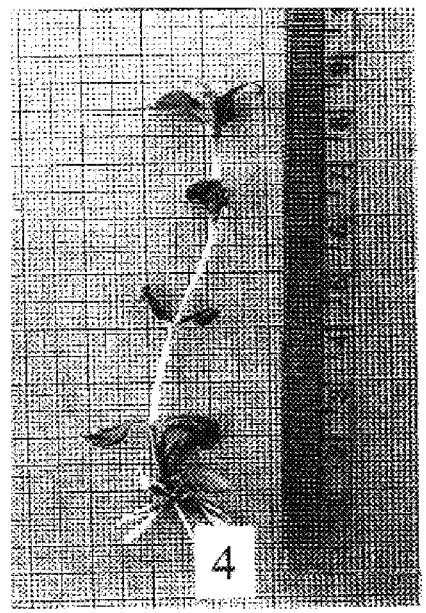
FIG. 4. Example of a well developed *Swertia chirata* plantlet propagated in vitro.
Figure 5A:
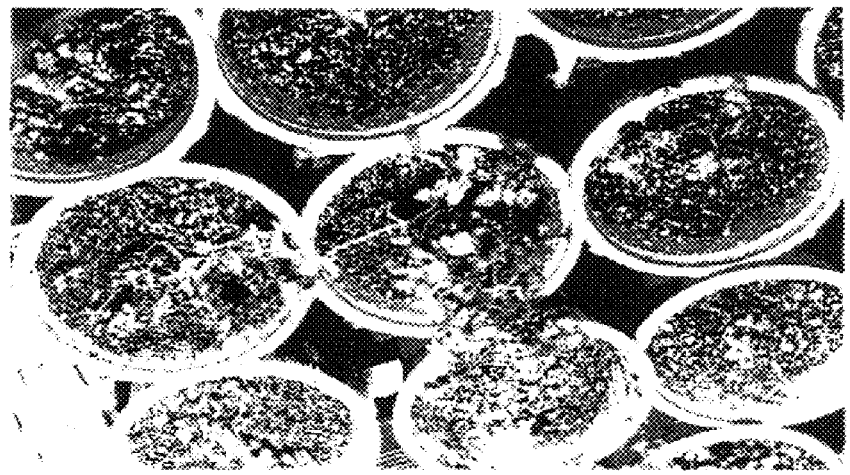
FIGS. 5A and 5B. Plants that were regenerated in vitro according to the invention after being transferred to soil comprising a 1:1 mixture of sterilized garden soil and vermiculite.
Figure 5B:
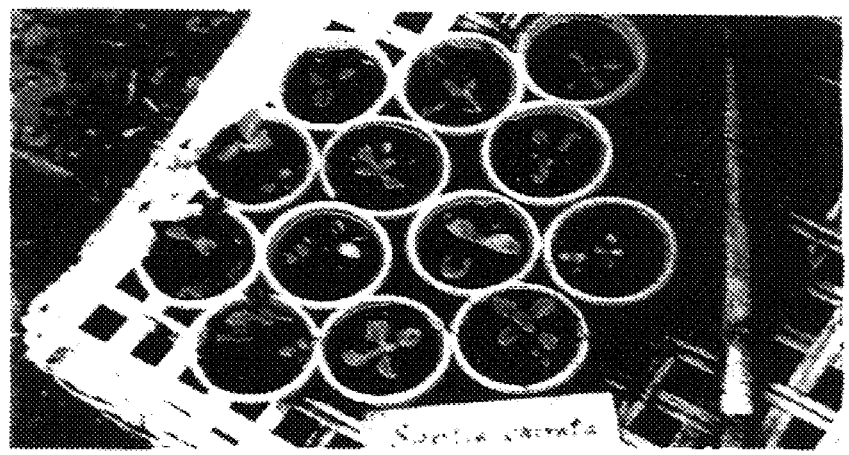

In the context of this disclosure, absent a contrary indication, the following definitions shall apply.

Cultivate—To grow, foster growth or propagate. The term is not limited with respect to developmental stage, but encompasses progression from any developmental stage to any other developmental stage.

Explant—A plant at any development stage, substantially free of contaminating microorganisms, suitable for culture in a nutrient medium.

Fast or Rapid—A healthy, robust *Swertia chirata* plant with a shoot length of from about 1 cm to 5 cm suitable for transplanting to soil may be produced in vitro from shoot apex or axillary bud explants in about 18 weeks or less.

In the wild—Cultivation and/or propagation "in the wild" primarily refers to outdoor growth of *Swertia* plants in an environment similar to *Swertia*'s native habitat substantially free of human manipulation. However, this term encompasses any environment wherein at least one or more of the following factors is not and/or cannot be controlled: temperature, humidity, photoperiod, light intensity, and exposure to microorganisms, herbivores, or pathogenic organisms.

Induce—To stimulate or support a response.

MS basal culture medium—Culture medium described by Murashige T and Skoog F (1965, Physiol Plant 15: 433–497), variants thereof known in the art, and MS basal culture medium I.

MS basal culture medium I—This comprises 1650 mg/L $NH_4NO_3$, 1900 mg/L $KNO_3$, 440 mg/L $CaCl_2.2H_2O$, 370 mg/L $MgSO_4.7H_2O$, 170 mg/L $KH_2PO_4$, 0.83 mg/L KI, 6.2 mg/L $H_3BO_3$, 16.9 mg/L $MnSO_4.4H_2O$, 8.6 mg/L $ZnSO_4.7H_2O$, 0.025 mg/L $Na_2MoO_4.2H_2O$, 0.025 mg/L $CuSO_4.5H_2O$, 0.025 mg/L $CoCl_2.6H_2O$, 0.5 mg/L nicotinic acid, 0.5 mg/L pyridoxine HCl, 0.1 mg/L thiamine, and 2 mg/L glycine. Variations of the indicated concentrations, if any, are preferably less than 5%. The pH is about 5.8.

Time—Period following initial contact with a media. For example, "weeks" may refer to the number of weeks after explants were first contacted with a medium.

General Remarks

The instant invention relates to in vitro cultivation of species of the genus *Swertia*, preferably *Swertia chirata*, more preferably *Swertia chirata* (Ham). The present invention is not limited to any particular variety or genotype but may be applied to genetically diverse varieties and species of *Swertia*.

The methods and compositions of the invention may be used to raise large populations of genetically heterogeneous *Swertia chirata* seedlings for reliable and effective in-situ and ex-situ conservation of this threatened species. The methods and compositions of the invention may also be used to cultivate *Swertia chirata* anywhere in the world during any season. Fast in vitro propagation of *Swertia chirata* according to the invention may allow wider utilization of its medicinal properties.

The instant invention represents the results of years of Applicants' effort. The concentration ranges of MS culture medium and hormones provided by the instant invention have been observed to be of critical importance. It is believed that any deviation from the same is unlikely to produce desired results.

The invention contemplates use of these methods and compositions for commercial bulk production of *Swertia chirata*. Bulk production may result in gram quantities of this plant and preferably kilogram quantities or more.

Materials

The invention contemplates the use of any plant cells, tissues or organs to initiate in vitro cultures. In some preferred embodiments, axillary buds and shoots apices are used since these tissues are the most regenerative and result in multi-fold increase in shoot proliferation. In some preferred embodiments, axillary shoot proliferation may be achieved using shoot apex and axillary shoot bud explants.

The invention provides a synergistic tissue culture media formulation to regenerate *Swertia chirata* shoot apices and axillary shoot bud explants in vitro. The formulation was found to be useful for regeneration of large number of tissue cultured plantlets of *Swertia chirata* in vitro via axillary shoot proliferation utilizing shoot apices and axillary shoot buds explants in vitro.

The culture media compositions of the invention are preferably homogeneous and may be used for culture initiation, shoot propagation, and root formation to produce a large number of *Swertia chirata* plants in vitro. The culture media compositions of the invention comprise Murashige and Skoog (MS) basal culture medium, varied concentrations of plant hormones, and other additives. Plant hormones may be selected from the group consisting of IAA, IBA, $GA_3$, BAP, and NAA. Additives include, for example, agar, sucrose, antibiotics, and antifungal agents. In preferred embodiments, the range of plant hormones is from about 0.5 mg/L to about 1.0 mg/L for BAP, from about 0.1 mg/L to about 1.0 mg/L for $GA_3$, from about 0.5 mg/L to about 1.0 mg/L for IAA, from about 0.5 mg/L to about 1.0 mg/L for IBA, and from about 0.5 mg/L to about 5.0 mg/L for α-NAA.

In some embodiments of the invention, a first or "initiation" medium comprises MS basal culture medium, from about 0.5 mg/L to about 1.0 mg/L BAP, optionally about 0.5 mg/L NAA, from about 0.5 mg/L to about 1.0 mg/L IAA, from about 0.5 mg/L to about 1.0 mg/L IBA, and from about 1% to about 3% sucrose. These compositions are capable of inducing or supporting initiation of an axillary bud and/or shoot apex explant culture. In some embodiments of the invention, the initiation medium comprises modified MS basal culture medium, about 0.5 mg/L BAP, and about 0.5 mg/L NAA. In some embodiments of the invention, the initiation medium comprises modified MS basal culture medium, about 1.0 mg/L BAP, and about 1.0 mg/L IAA.

In some embodiments of the invention, a second or "shoot proliferation" medium comprises MS basal culture medium, optionally from about 0.5 mg/L to about 1.0 mg/L BAP, about 1.0 mg/L IAA, about 1.0 mg/L $GA_3$, and from about 1% to about 3% sucrose. These compositions are capable of inducing or supporting a high shoot proliferation and development with shoot multiplicity rages from about 11.4 to about 26.25 and shoot length ranges from less than 1 cm to about 5 cm.

In some preferred embodiments, the shoot proliferation medium comprises modified MS basal culture medium, about 1 mg/L IAA, and about 3% sucrose. This medium is capable of inducing or supporting shoot proliferation with a shoot multiplicity of about 20.3 and shoot length ranging from about 2.5 cm to about 3.0 cm.

In some embodiments, the shoot proliferation medium comprises modified MS basal culture medium, about 1 mg/L IAA, and about 1% sucrose. This medium is capable of inducing or supporting shoot proliferation with a shoot multiplicity of about 11.4.

In some embodiments, the shoot proliferation medium comprises modified MS basal culture medium, about 1 mg/L IAA, and about 2% sucrose. This medium is capable of inducing or supporting shoot proliferation with a shoot multiplicity of about 11.8.

In some preferred embodiments, the shoot proliferation medium comprises modified MS basal culture medium, about 0.5 mg/L BAP, and about 1.0 mg/L $GA_3$. This medium is capable of inducing or supporting shoot proliferation with a shoot multiplicity of about 26.25 and shoot length ranging from about 1 cm to about 5 cm.

In some preferred embodiments, the shoot proliferation medium comprises modified MS basal culture medium, about 0.5 mg/L BAP, about 1.0 mg/L IAA, and about 3% sucrose. This medium is capable of inducing or supporting shoot proliferation with a shoot multiplicity of about 21.2 and shoot length ranging from about 1 cm to about 5 cm.

In some embodiments of the invention, a third or "rooting" medium comprises MS basal culture medium, optionally plant hormones selected from the group consisting of from about 1.0 mg/L to about 5.0 mg/L NAA, from about 1.0 mg/L to about 5.0 mg/L IAA, and from about 1.0 mg/L to about 5.0 mg/L IBA, and from about 1% to about 3% sucrose. These compositions are capable of inducing or supporting efficient development of the root system. Rooting percentages for compositions of the invention range between 50% to 80% at from about 8 weeks to about 10 weeks.

In some preferred embodiments, the rooting medium comprises modified MS basal culture medium and from about 1.0 mg/L to about 5.0 mg/L IAA. This medium is capable of inducing or supporting from about 75% to about 80% rooting at about 8 weeks. These roots are well-developed, white colored and thick.

In some embodiments, the rooting medium comprises modified MS basal culture medium and from about 1.0 mg/L to about 5.0 mg/L IBA. This medium is capable of inducing or supporting from about 60% to about 65% rooting at about 8 weeks. These roots are white colored, thick, and short.

In some embodiments, the rooting medium comprises modified MS basal culture medium and from about 1.0 mg/L to about 5.0 mg/L NAA. This medium is capable of inducing or supporting from about 50% to about 60% rooting at about 10 weeks. These roots are brown colored, sparsely developed, and lack hairs.

In one embodiment of the invention, the media of Table 1 is used for establishment of cultures using shoot apices and axillary bud explants, proliferation of multiple shoots, and rooting regenerated shoots. The seedlings or plantlets so produced are suitable for transfer to soil.

TABLE 1

Tissue Culture Media Formulation for various stages involved in propagation of *Swertia chirata*:

| Constituents | Establishment of Cultures (mg/L) | Proliferation of shoots/Development (mg/l) | Rooting of Shoots (mg/l) |
| --- | --- | --- | --- |
| $MgSO_4.7H_2O$ | 370 | 370 | 370 |
| $MnSO_4.H_2O$ | 16.9 | 16.9 | 16.9 |
| $ZnSO_4.7H_2O$ | 8.6 | 8.6 | 8.6 |
| $KNO_3$ | 1900 | 1900 | 1900 |
| $NH_4NO_3$ | 1650 | 1650 | 1650 |
| $CaCl_2.2H_2O$ | 440 | 440 | 440 |
| $KH_2.PO_4$ | 170 | 170 | 170 |
| $H_3BO_3$ | 6.2 | 6.2 | 6.2 |
| KI | 0.83 | 0.83 | 0.83 |
| $CuSO_4.5H_2O$ | 0.025 | 0.025 | 0.025 |
| $CoCl_2.6H_2O$ | 0.025 | 0.025 | 0.025 |
| $NaMoO_4.2H_2O$ | 0.025 | 0.025 | 0.025 |
| Glycine | 2 | 2 | 2 |
| Thiamine HCl | 0.1 | 0.1 | 0.1 |
| Pyridoxine-HCl | 0.5 | 0.5 | 0.5 |
| Nicotinic acid | 0.5 | 0.5 | 0.5 |
| PH | 5.8 | 5.8 | 5.8 |
| Supporting system | Agar (0.8%) | i) Agar (0.8%) ii) Liquid | Agar (0.8%) |
| Benzyladenine (BAP) | 0.5–1.0 | 0.5–1.0 | — |
| Gibbrellic acid ($GA_3$) | — | 1.0 | — |
| Indoleacetic acid (IAA) | 0.5–1.0 | 1.0 | 1.0 |
| Indole butyric acid (IBA) | 0.5–1.0 | — | 1.0 |
| Naphthalene acetic acid (NAA) | 0.5 | — | 1.0 |
| Sucrose | 1–3% | 1–3% | 1–3% |

Methods

The invention contemplates the use of standard techniques related to in vitro cultivation of plants. See e.g. Gelvin S B, Schilperoort R A, Verma D P S, eds., *Plant Molecular Biology Manual, 2nd edition*, Klewer 1994; Clark M, ed., *Plant Molecular Biology*, Springer Verlag 1997; Jones P, ed., *Plant Molecular Biology*, John Wiley & Son Ltd 1997. One of ordinary skill in the art will appreciate that techniques developed for in vitro cultivation and propagation of lily, Arabidopsis, tobacco, rice and other plants may be useful for practicing the instant invention. Unless otherwise specified, all in vitro methods were performed using appropriate aseptic techniques known to those of ordinary skill in the art, such as use of Laminar air flow.

The present invention provides a method for multi-fold increased in vitro propagation of *Swertia chirata* comprising:

cleaning various explants viz. root, stem, apical and axillary buds-with-nodes of said plant;

sterilizing cleansed explants;

treating replicates of 10 explants comprising shoot apices, axillary buds, stem segments seedlings, and leaf segments;

using about 0.8% Agar as support system;

testing the efficacy of various explants cultured on first media culture compositions comprising modified MS basal culture media and BAP ranging between 0.5 to 1.0 mg/L, and optionally containing NAA about 0.5 mg/L, IAA ranging between 0.5 to 1.0 mg/L, IBA ranging between 0.5 to 1.0 mg/L, and sucrose ranging between 1 to 3%, supplemented with various plant growth regulators, to find an efficient explant source for culture initiation;

measuring the effect of various second media compositions comprising modified MS basal culture medium, and optionally containing BAP ranging between 0.5 to 1.0 mg/L, IAA about 1.0 mg/L, $GA_3$ about 1.0 mg/L, and sucrose concentration ranging between 1 to 3%, on shoot multiplication and shoot development after about every 4 weeks;

excising the shoot developed in above-mentioned cultures;

using excised shoots to find the best or a satisfactory second media composition for shoot multiplication;

incubating the above-mentioned cultures at 20° C. under 8/12 hr light and dark period;

subculturing after about every 4 weeks for the respective media formulations;

excising four weeks long shoot obtained as above;

transferring excised shoots into modified MS basal culture medium with varied concentrations of several auxins ranging between 1 and 5 mg/L, selected from a group comprising IAA, IBA, and NAA;

using excised roots to find the best or a satisfactory third media composition comprising modified MS basal culture medium, optionally containing plant hormones selected from a group consisting of IAA ranging between 1.0 to 5.0 mg/L, IBA ranging between 1.0 to 5.0 mg/L, NAA ranging between 1.0 to 5.0 mg/L, and sucrose concentration ranging between 1 to 3%, for well developed rooting system; and transferring the above-mentioned in vitro grown plant species *Swertia chirata* into varied potting mixtures, showing about 70% survival rate with vermiculite and sterilized garden soil in ratio 1:1.

Explants are preferably transferred using standard plant tissue culture aseptic techniques. Aseptic techniques are typically unnecessary for transferring plantlets to soil.

Initiation

Naturally growing live *Swertia chirata* plant material from different locations in the Darjeeling hills of India may be collected and identified. Various explants, e.g. root, stem, apical and axillary buds-with-nodes from collected plants may be surface sterilized before initiating primary in vitro cultures. The efficacy of various explants cultured on different media combinations and supplemented with various plant growth regulators may be tested to find out efficient explant source for culture initiation. Each treatment may consist of replicates, e.g. 10, of different explants (shoot apices, axillary buds, stem segments seedlings, leaf segments). Axillary buds and shoot apices cultured on media described in Table 1 are the most regenerative and resulted shoot proliferation (FIG. 1). A combination of modified MS+BAP (0.5 modified MS)+NAA (0.5 mg/L) and modified MS+BAP(1 mg/L)+IAA (1 mg/L) are most responsive treatments (FIG. 1).

Shoot Proliferation

The effect of various media combinations on shoot multiplication and shoot development (after 4 weeks) may be tested. The excised shoots developed in primary cultures may be cultured on media to test the effect of a range of concentration of various plant growth regulators, adenine sulphate, gibberellic acid, supplemented to modified MS basal medium to find the best or a satisfactory treatment for shoot multiplication. The cultures may be incubated at 20° C. under 8/12 hr light and dark period. Subcultures may be done after every 4 weeks on the same media formulation.

Table 2 shows the influence of various treatment on shoot number and length.

TABLE 2

Effect of various media combinations on shoot multiplication and shoot development (After 4 weeks)

| Media BM* + mg/L | Shoot number Shoots/Culture | Shoot length (cm) |
| --- | --- | --- |
| modified MS + 0.5 BAP | 3.6 | <1 |
| modified MS + 1.0 IAA + 1% sucrose | 11.4 | <1 |
| modified MS + 1.0 IAA + 2% sucrose | 11.8 | <1 |
| modified MS + 1.0 IAA + 3% sucrose | 20.3 | 2.5–3.0 |
| ½ modified MS + 1.0 IAA + 0.5 mg BAP + 3% sucrose | 21.2 | <1 |
| ½ modified MS + 1.0 IAA + 0.5 mg BAP + 3% sucrose | 6.6 | <1 |
| modified MS + 1.0 IAA + 5 mg glutamine + 3% sucrose | 1.2 | <1 |
| modified MS + 1.0 IAA + 0.5 mg BAP + 3% sucrose | 5.4 | <1 |
| modified MS + 1.0 IAA + Ads 10 mg | 4.2 | <1 |
| modified MS + 1.0 IAA + Ads 20 mg | 6.8 | <1 |
| modified MS + 0.5 mg BAP + $GA_3$ 1 mg | 26.25 | 1–5 |

Modified MS basal medium+(1.0 mg/L IAA+3% sucrose) and modified MS basal medium+[0.5 mg BAP+$GA_3$ (1 mg/L)] results in maximum shoot proliferation and shoot development.

Rooting

The effect of various auxins on rooting percent and duration may be studied using four-week shoots obtained in the preceding section.

The excised shoot may be transferred to modified MS basal culture medium with varied concentrations of several auxins selected from a group comprising IAA, IBA, and NAA as shown in Table 3.

TABLE 3

Rooting percent and duration as influenced by different auxins

| Auxins$^{BM+mg.l-1}$ | Rooting % | Rooting (wks) |
| --- | --- | --- |
| IAA* | | |
| 1 | 80 | 8 |
| 2 | 75 | 8 |
| 5 | 75 | 8 |
| IBA** | | |
| 1 | 60 | 8 |
| 2 | 62 | 8 |
| 5 | 60 | 8 |
| NAA*** | | |
| 1 | 50 | 10 |
| 2 | 50 | 10 |
| 5 | 60 | 10 |

Root morphology
*White-thick, well developed root system
**Whitish thin with short roots
***Brownish sparsely developed roots without root hairs.

Media containing IAA (1 mg/L) fosters maximum rooting percentage and results in white colored, thick and well developed root system.

Transfer to Soil

In some embodiments of the invention, in vitro cultivated plants may be transferred to soil. The survival rate of *Swertia chirata* is about 70% in soil comprising a 1:1 mixture of vermiculite and sterilized garden soil. The survival rate is about 50% in soil comprising either vermiculite alone or a 1:1 mixture of soilrite and sterilized garden soil.

The effect of different potting mixtures on in vitro raised plantlets may be determined by transferring the plantlets obtained in the preceding section to soil. Examples of various soils are provided in Table 4.

TABLE 4

Effect of different Potting Mixture on in vitro raised plantlets

| Potting Mixture Comprising: | Survival % |
|---|---|
| Soilrite + Garden soil (1:1) | 20 |
| Vermiculite + Garden soil (1:1) | 20 |
| Peatmoss + Garden soil (1:1) | 0 |
| Garden soil | 8 |
| Garden soil (Sterilized) | 20 |
| Sand | 40 |
| Soilrite + Perlite (10:1) | 30 |
| Vermiculite | 50 |
| Peatmoss | 0 |
| Soilrite + Garden soil (1:1) Sterilized | 50 |
| Vermiculite + Garden soil (1:1) Sterilized | 70 |
| Peatmoss + Garden soil (1:1) | 40 |

Garden soil is the mixture of soil found in the forest area.

The best percentage of plantlet survival is observed in polyhouse where vermiculite and garden soil are used in the ratio of 1:1.

EXAMPLES

The present invention is illustrated, but not limited, by the following examples. Other examples and embodiments will be apparent to those skilled in the art and do not depart from the spirit and scope of the invention.

Example 1

The experiment consisted of 10 treatments in the form of various combination of benzyladenine (BA 0.5-mg/c), IAA, IBA, and et-NAA supplemented to modified MS based culture medium with 0.8% agar by weight.

Each treatment consisted of 10 replicates of different explants (shoot apices, axillary buds, stem segments seedlings, leaf segments).

Axillary buds and shoot apices cultured on media described in Table 1 were most regenerative and resulted shoot proliferation (FIG. 1).

Combination of modified MS+BAP (0.5 ms)+NAA (0.5 mg/L) and modified MS+BAP (1 mg/L)+IAA(1 mg/L) were most responsive treatments (FIG. 1).

Example 2

In this experiment the shoot developed in primary cultures were excised and cultured on media to test the effect of a range of concentration of various plant growth regulators, adenine sulphate, gibberellic acid, supplemented to modified MS basal medium to find the best or a satisfactory treatment for shoot multiplication.

The cultures were incubated at 20° C. under 8/12 hr light and dark period. Subculture was done after every 4 weeks on the same media formulation.

The results in Table 2 show the influence of various treatment on shoot number and length.

Among the tested combinations modified MS basal medium+(1.0 mg/L IAA+3% and 0.5 mg BAP+GA3 (1 mg/L) resulted maximum shoot proliferation and better shoot development.

Example 3

In this experiment there are 3 treatments of auxin IAA, IBA and NAA using various levels (1–5 mg/L) supplemented to modified MS media, Supporting system Agar (0.8%).

Four weeks long shoot achieved in experiment 2 were excised and transferred to above referred medium The results in Table 3 show the influence of various treatment on rooting percentage and duration as influenced by respective treatment and concentration.

Media containing IAA (1 mg/L) fostered maximum rooting percentage and resulted white thick were root system.

Example 4

Rooted plantlets of Example 3 were transferred to different potting mixtures. Better percentage of plantlets survived in polyhouse where vermiculite and garden soil (1:1 ratio) were used (Table 4).

The references cited throughout this application are incorporated herein in their entirety by reference.

We claim:

1. A culture medium comprising 1650 mg/L $NH_4NO_3$, 1900 mg/L $KNO_3$, 440 mg/L $CaCl_2.2H_2O$, 370 mg/L $MgSO_4.7H_2O$, 170 mg/L $KH_2PO_4$, 0.83 mg/L KI, 6.2 mg/L $H_3BO_3$, 16.9 mg/L $MnSO_4.4H_2O$, 8.6 mg/L $ZnSO_4.7H_2O$, 0.025 mg/L $Na_2MoO_4.2H_2O$, 0.025 mg/L $CuSO_4.5H_2O$, 0.025 mg/L $CoCl_2.6H_2O$, 0.5 mg/L nicotinic acid, 0.5 mg/L pyridoxine HCl, 0.1 mg/L thiamine, and 2 mg/L glycine, from about 0.5 mg/L to about 1.0 mg/L benzyladenine, from about 0.5 mg/L to about 1.0 mg/L IAA, from about 0.5 mg/L to about 1.0 mg/L IBA, about 0.5 mg/L NAA, and from about 1% to about 3% sucrose by weight and having a pH of about 5.8.

2. The culture medium of claim 1 further comprising about 0.8% agar by weight.

3. A culture medium comprising 1650 mg/L $NH_4NO_3$, 1900 mg/L $KNO_3$, 440 mg/L $CaCl_2.2H_2O$, 370 mg/L $MgSO_4.7H_2O$, 170 mg/L $KH_2PO_4$, 0.83 mg/L KI, 6.2 mg/L $H_3BO_3$, 16.9 mg/L $MnSO_4.4H_2O$, 8.6 mg/L $ZnSO_4.7H_2O$, 0.025 mg/L $Na_2MoO_4.2H_2O$, 0.025 mg/L $CuSO_4.5H_2O$, 0.025 mg/L $CoCl_2.6H_2O$, 0.5 mg/L nicotinic acid, 0.5 mg/L pyridoxine HCl, 0.1 mg/L thiamine, and 2 mg/L glycine, from about 0.5 mg/L to about 1.0 mg/L BAP, about 1.0 mg/L $GA_3$, about 1.0 mg/L IAA, and from about 1% to about 3% sucrose by weight and having a pH of about 5.8.

4. The culture medium of claim 3 further comprising about 0.8% agar by weight.

5. A culture medium comprising 1650 mg/L $NH_4NO_3$, 1900 mg/L $KNO_3$, 440 mg/L $CaCl_2.2H_2O$, 370 mg/L $MgSO_4.7H_2O$, 170 mg/L $KH_2PO_4$, 0.83 mg/L KI, 6.2 mg/L H$_3$BO$_3$, 16.9 mg/L MnSO$_4$.4H$_2$0, 8.6 mg/L ZnSO$_4$.7H$_2$0, 0.025 mg/L Na$_2$MoO$_4$.2H$_2$0, 0.025 mg/L CuSO$_4$.5H$_2$O, 0.025 mg/L CoCl$_2$.6H$_2$0, 0.5 mg/L nicotinic acid, 0.5 mg/L pyridoxine HCl, 0.1 mg/L thiamine, and 2 mg/L glycine, from about 1.0 mg/L to about 5.0 mg/L IAA, from about 1.0 mg/L to about 5.0 mg/L IBA, from about 1.0 mg/L to about 5.0 mg/L NAA, and from about 1% to about 3% sucrose by weight and having a pH of about 5.8.

6. The culture medium of claim 5 further comprising about 0.8% agar by weight.

* * * * *